United States Patent [19]
DePasquale

[11] Patent Number: 5,620,009
[45] Date of Patent: Apr. 15, 1997

[54] APPLIANCE AND METHOD FOR THE DIAGNOSIS AND TREATMENT OF SCOLIOSIS

[76] Inventor: Carmelo DePasquale, Via Pappa Giovanni XXIII, 160, Barcellona Pozzo Di Gotto (ME), Italy

[21] Appl. No.: 504,913

[22] Filed: Jul. 20, 1995

[30] Foreign Application Priority Data

Jul. 28, 1994 [IT] Italy .................................. ME94A0013

[51] Int. Cl.⁶ .................................................. A61B 5/103
[52] U.S. Cl. ............................................................ 128/781
[58] Field of Search .............................. 128/870, 781.2, 128/707, 845, 846, 774; 602/19

[56] References Cited

U.S. PATENT DOCUMENTS 41,548  2/1864  Taylor ........................................ 602/19

FOREIGN PATENT DOCUMENTS 9315657  8/1993  Italy .......................................... 128/781
1109128  8/1984  U.S.S.R. .................................. 128/781

*Primary Examiner*—Max Hindenburg
*Assistant Examiner*—Pamela L. Wingood
*Attorney, Agent, or Firm*—Leonard Bloom

[57] ABSTRACT

An appliance for the diagnosis and treatment of scoliosis of a patient includes a supporting base sustaining a vertical polarized light screen, a seat and a monitor. A closed circuit camera behind the polarized light screen films a picture that appears on the polarized light screen which corresponds to the patient's spine, when he (or she) sits on the seat and holds his (or her) back flat against the polarized light screen. The picture is projected onto the monitor, such that the patient can see a visualization of his (or her) spine on the monitor in real time. This allows a real time identification of the precise location of the scoliosis and facilitates in performing corrective exercises.

19 Claims, 2 Drawing Sheets

APPLIANCE AND METHOD FOR THE DIAGNOSIS AND TREATMENT OF SCOLIOSIS

BACKGROUND OF THE INVENTION

1. Field of the Invention

This patent application concerns an appliance for the diagnosis and treatment of scoliosis.

2. Description of the Prior Art

By definition, scoliosis is a lateral curvature of the spine that deforms the chest cavity producing a bulge towards the back known as the gibbus or hump.

This is a very common pathology that is generally classed as a congenital or acquired change, rather than an illness. Acquired scoliosis is today extremely widespread, above all in children and teenagers, as a result of the heavy books that they carry in their rucksacks.

Scoliosis is currently diagnosed mainly by x-rays investigations that are extremely accurate but have the disadvantage, especially in the case of repeated investigations, of exposing the patient to harmful radiation.

The best therapy for scoliosis is still considered to be exercising which is usually carried out against prescription of the treating orthopaedic surgeon.

Gym exercises however do not always give the desired result of removing or at least reducing the gibbus.

The reason for this is that often the exercises prescribed are very general and not specific for a particular form of scoliosis; in addition, more often than not they are not correctly performed by the patient.

SUMMARY OF THE INVENTION

The purpose of this invention is to design an appliance that not only provides an accurate diagnosis of the form of scoliosis in question but also helps and guides the patient in performing the most suitable correction exercises.

The appliance according to the invention consists of a coloured polarised light screen of the type used in orthopaedics to show flat or claw feet.

Screens of this type make it possible to show the shape of the foot and extension of the contact surface between the skin and the screen, very accurately and clearly; the area of the body touching this screen is shown as a zone in the same colour as the polarised light.

This screen, in the appliance according to the invention, is held vertically by means of a metal frame having a seat in front for the patient who places his back flat against the polarised light screen.

The picture that appears on the back of the polarised light screen, and which obviously corresponds to the exact divergence of the patient's spine and consequently the precise position of the gibbus—is filmed by a miniature closed circuit camera onto a video in front of the patient. The patient can therefore verify in real time the exact condition of his spine.

As mentioned above however, this appliance according to the invention is not only designed for purposes of diagnosis but also as an extremely important therapeutic and corrective aid.

Two handles being provided on the sides of the monitor, in front of the patient, that the patient uses to perform the exercises required to correct the divergence of the upper spine.

Under the monitor, in front of the patient, handlebars having a horizontal axis are provided that the patient presses against with his knees to perform the exercises for correcting the divergence of the lower spine.

The inventive idea behind this appliance is that of allowing the patient to perform exercises, by means of the handlebars, for his specific requirements while verifying that the position for the exercises is correct, in real time, by means of a technique known as "bio feedback".

If the patient keeps his back flat against the screen of the scoliograph, he can verify immediately the precision and efficiency of the corrective exercises performed with respect to the divergence of his spine on the monitor that films the images of the polarised light screen.

By allowing the patient to follow the exercises on the monitor step by step, the same can clearly perform only those exercises which correct the specific divergence of his spine while avoiding unnecessary or even harmful exercises.

More specifically, by exercising, the patient attempts to change the divergence of his spine so that symmetric coloured spots with respect to a vertical axis appear on the polarised light screen that will only appear when the divergence of the spine has been adequately corrected.

Moreover, in order to allow the patient to align his shoulders perfectly before and during the corrective exercises, the appliance according to the invention is also equipped with a mirror above the video facing the patient seated against the polarised light screen.

BRIEF DESCRIPTION OF THE DRAWINGS

For major clarity the description of the invention continues with reference to the enclosed drawings which are intended for purposes of illustration and not in a limiting sense, whereby.

DESCRIPTION OF THE PREFERRED EMBODIMENT

Figure 1:
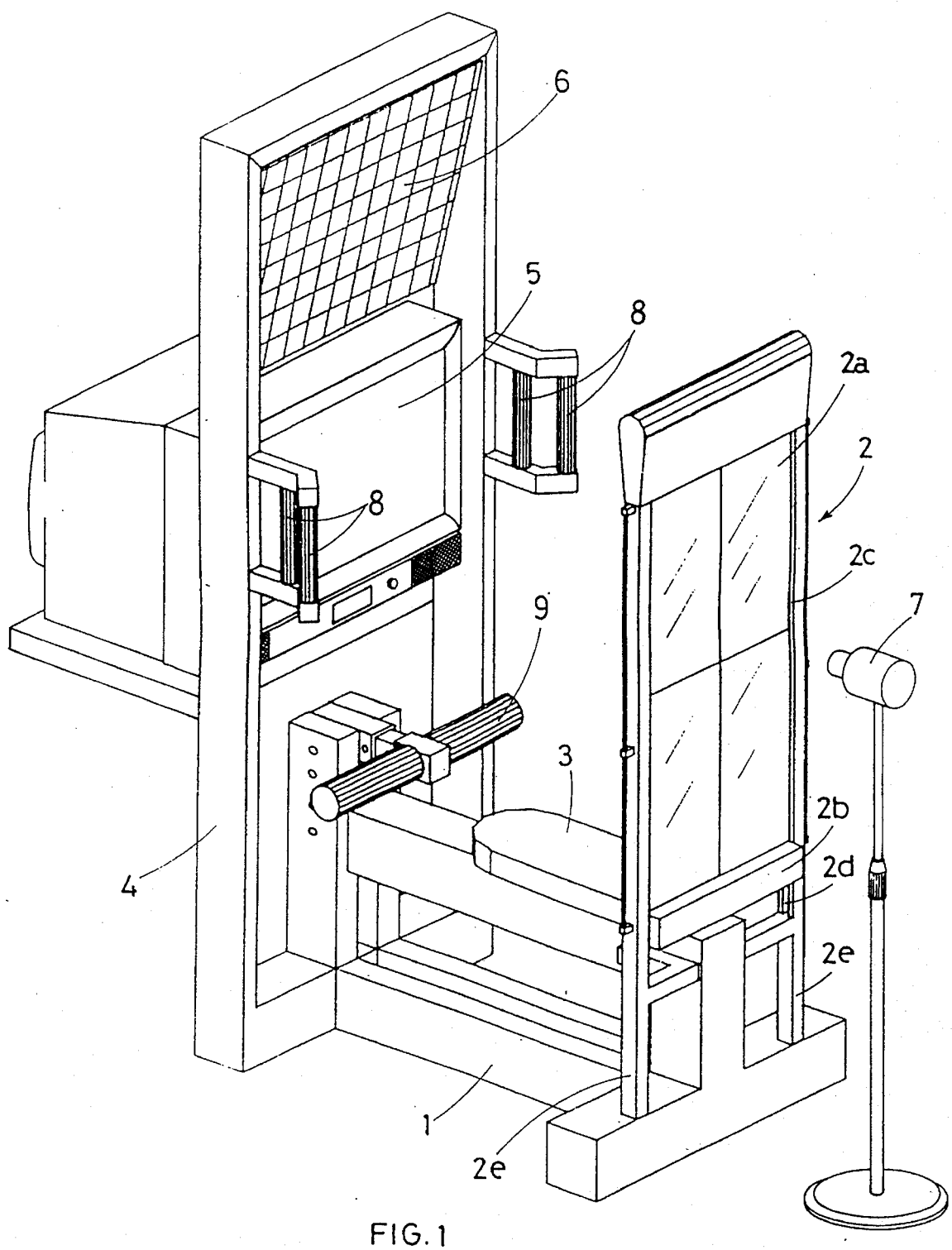
FIG. 1 is an axonometric view of the appliance according to the invention.

With reference to FIG. 1, the appliance according to the invention consists of a metal base (1) supporting a polarised light screen (2) at one end, with seat (3) and a supporting frame (4) at the other end to support a monitor (5) and a adjustable overhead mirror (6).

A closed circuit camera (7) that films the images appearing on the screen and projects them on the above monitor (5) and reproduces them for the patient, being provided in front of the screen (2)—opposite the side on which the patient is seated.

The appliance according to the invention also being provided with a pair of handles (8) applied to the uprights of the supporting frame (4), fitted on the sides of the monitor (5) as well as handlebars (9) having a horizontal axis, placed at the centre and under the monitor (5), for knee exercises.

The handlebars (9) being designed to slide backwards and forwards so as to regulate the distance from the seat (3); the handlebars (9) also being height adjustable.

The polarised light screen (2) consists basically of a thick glass (2a) under whose bottom horizontal edge a box (2b) containing he light source, is applied.

The top of the box (2b) having a longitudinal slot aligned perfectly with the edge of the glass (2a) from which a blade of polarised light projects to light the glass (2a) from bottom to top and for its entire height.

This glass (2a) being delimited by a metal frame (2c) and sliding vertically in two grooves (2d) on the internal face of the uprights of the main support frame (2e), making it possible to regulate the height of said screen (2) with respect to the seat (3) according to the height of the patient.

Figure 2:
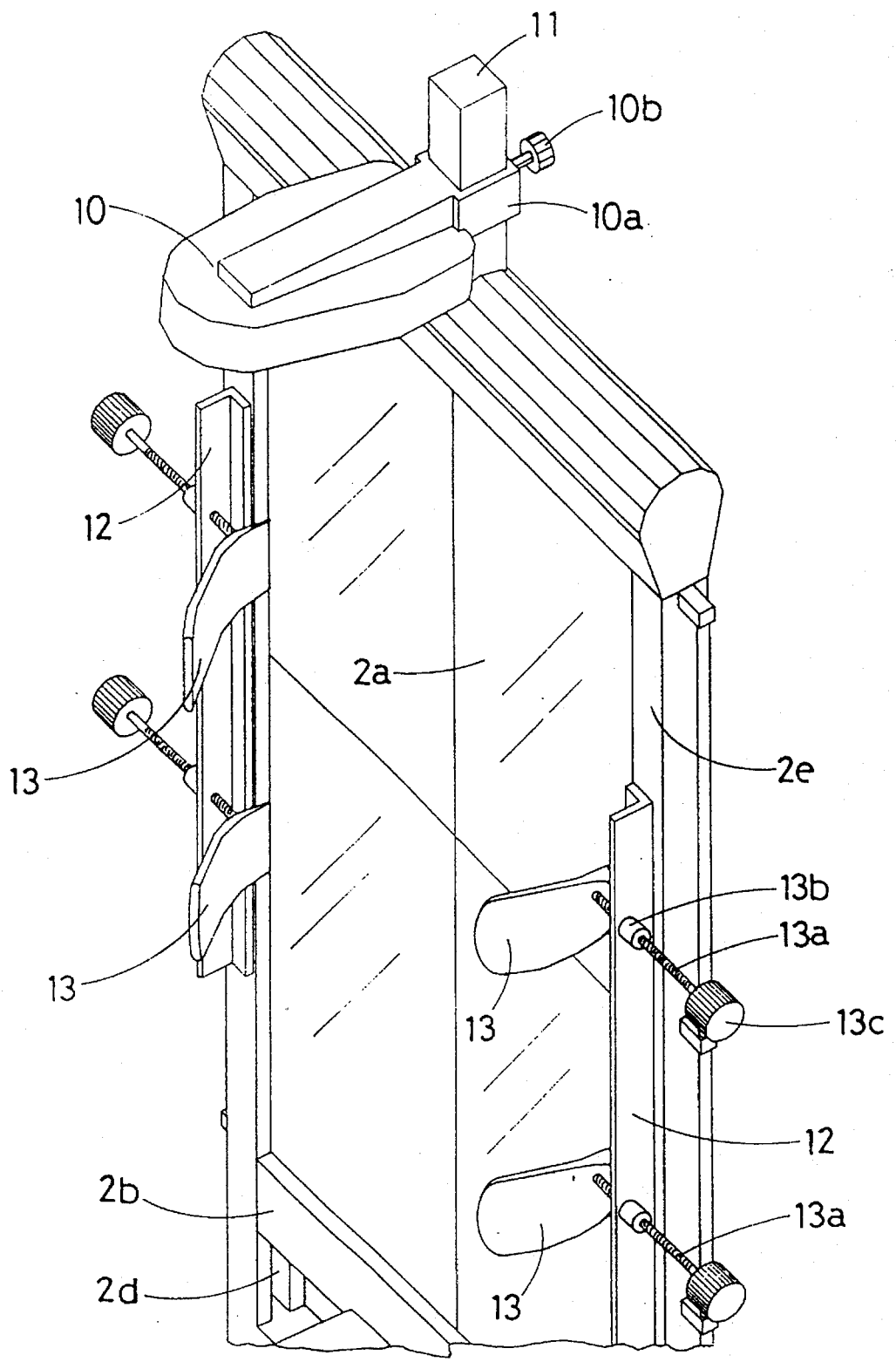
FIG. 2 is an axonometric view of a preferred embodiment of the polarised light screen used with the appliance according to the invention.

With specific reference to FIG. 2, the appliance according to the invention includes a number of accessories applied to the fixed frame (2e) of the polarised light screen (2) in order to increase its versatility with respect to special corrective requirements of a patient.

The first of these accessories is a shelf (10) mounted horizontally at the top of the screen (2) and positioned precisely above the seat (3); said shelf (10) being designed to allow the patient to push against the same with his head in order to stretch the spine.

The enclosed figure shows that said plate (10) is characterised by a rear coupling (10a) sliding along a vertical pin (11) that can be fixed at the required height thanks to a screw with knob (10b).

Two "L" shaped vertically sliding brackets (12) supporting two pairs of thrusting elements (13) at the two sides of the screen (2) being mounted on the uprights of the frame (2e) supporting the glass (2a).

These are four elements (13) aligned in horizontal pairs at two different levels against which the patient pushes with his trunk, either towards the left or towards the right—according to the required correction.

The vertical sliding of the two slides (12) supporting the two pairs of elements (13) makes it possible to regulate their height—with respect to the seat (3) and the screen (2)—according to the physical characteristics of the patient.

In addition, each of said elements (13) is fixed at the end of a horizontal threaded rod (138a) screwed into a threaded bushing (13b) applied on one of the two brackets (12).

The number (13c) has been used to indicate the operating knobs of the four rods (13a).

This feature naturally ensures that it is possible to draw the pairs of elements (13) closer or further from the body of the patient, again according to the physical characteristics of the same.

I claim:

1. An appliance for the diagnosis and treatment of scoliosis of a patient, characterized by a supporting base (1) sustaining a polarized light screen (2) at one end positioned vertically at the back of a seat (3) and by a supporting frame (4) at the other end, sustaining a monitor (5) facing the seat (3); the back of the screen (2) being equipped with a closed circuit camera (7) for filming a picture appearing on the screen (2) and connected to the above monitor (5) for visualization of said picture thereon; a pair of rigid handles (8) being applied to the uprights of the supporting frame (4) as well as r handlebars (9) having a horizontal axis positioned opposite the seat (3), wherein the patient, being seated on the seat (3), touches the polarized light screen (2) with his (or her back, such that the picture of the patient's spine appears on the screen (2), and such that the patient watches, in real time, a visualization of his (or her) spine on the monitor (5), thereby allowing the patient to identify the precise location of the scoliosis and thereby facilitating in performing corrective exercises as the patient pushes against the handles.

2. An appliance for the diagnosis and treatment of scoliosis of a patient characterized by a supporting base (1) sustaining a polarized light screen (2) at one end positioned vertically at the back of a seat (3) and by a supporting frame (4) at the other end, sustaining a monitor (5) facing the seat (3); the back of the screen (2) being equipped with a closed circuit camera (7) for filming a picture appearing on the screen (2) and connected to the above monitor (5) for visualization of said picture thereon; a pair of handles (8) being applied to the uprights of the supporting frame (4) as well as rigid handlebars (9) having a horizontal axis positioned opposite the seat (3)

wherein the patient, being seated on the seat (3), and touching the polarized light screen (2) by his (or her) back, watches, in real time a visualization of his (or her) spine on the monitor (5), wherein the polarized light screen (2) consists of a thick glass (2a) having under its bottom horizonal edge, a box (2b) containing a light source, featuring a longitudinal slot perfectly aligned with the edge of the above glass (2a).

3. The appliance for the diagnosis and treatment of scoliosis according to claim 1, characterised in that the glass (2a) of the polarised light screen (2) is delimited by a metal frame (2c) sliding vertically within two grooves (2d) on the internal face of the uprights of the fixed support frame (2e) applied directly to the supporting base (1).

4.) The appliance for the diagnosis and treatment of scoliosis according to claim 1) characterised by a horizontal-axis shelf (10) mounted at the top of the screen (2) and positioned exactly above the seat (3); said shelf (10) being supported by a coupling (10a) by means of screw and threaded fastening knob (10b), sliding in a vertical pin (11) applied at the top of the fixed frame supporting the screen (2).

5.) The appliance for the diagnosis and treatment of scoliosis, according to claim 1, characterised by two "L" shaped brackets (12) sliding vertically along the uprights of the fixed frame (2d) of the screen (2) to support the adjustable thrusting elements (13).

6. An appliance for the diagnosis and treatment of scoliosis of a patient, characterized by a supporting base (1) sustaining a polarized light screen (2) at one end positioned vertically at the back of a seat (3) and by a supporting frame (4) at the other end sustaining a monitor (5) facing the seat (3); the back of the screen (2) being equipped with a closed circuit camera (7) for filming a picture appearing on the screen (2) and connected to the above monitor (5) for visualization of said picture thereon; a pair of handles (8) being applied to the uprights of the supporting frame (4) as well as rigid handlebars (9) having a horizontal axis positioned opposite the seat (3); and an adjustable mirror (6) mounted above the monitor (5) and facing the seat (3); wherein the patient, being seated on the seat (3) and touching the polarized light screen (2) by his (or her) back, watches, in real time, visualization of his (or her) spine on the monitor (5).

7. An appliance for diagnosis and treatment of scoliosis of a patient, comprising:

a polarized light screen having a back, a monitor spaced apart from the polarized light screen, and a closed circuit camera for filming, in real time, images appearing on the back of the polarized light screen and simultaneously projecting said images onto the monitor;

whereby, once the patient's back presses against the polarized light screen, the image of the patient's spine immediately appears on the monitor in front of the patient, thereby allowing the patient to identify the precise location of the scoliosis and thereby facilitating in performing corrective exercises as the patient pushes against the handles.

8. The appliance of claim 7, wherein the polarized light screen is a vertically positioned thick glass screen, having a horizontal bottom edge, wherein a box containing a light source is positioned at the horizontal bottom edge, wherein said box has a longitudinal slot precisely aligned with the horizontal bottom edge of the screen for allowing the light out of the box for lighting the entire surface of the polarized light screen.

9. The appliance of claim 7, further comprising a supporting base sustaining the polarized light screen at one end thereof, and further sustaining a supporting frame at another end thereof; the supporting frame sustaining the monitor;

wherein a seat is provided between the polarized light screen and the supporting frame, such that the patient can sit while pressing against the polarized light screen with his (or her) back.

10. The appliance of claim 9, wherein a pair of rigid handles are applied to the uprights of the supporting frame, one from each side of the monitor, for being grasped by the patient to perform corrective exercises for the upper spine.

11. The appliance of claim 9, further comprising rigid horizontal handlebars under the monitor and opposite to the seat for being pressed by the patient's knees to perform corrective exercises for the lower spine.

12. The appliance of claim 11, wherein the horizontal handle bars are height adjustable.

13. The appliance of claim 11, wherein a distance between the horizontal handlebars and the seat is adjustable.

14. The appliance of claim 7, further comprising an adjustable mirror mounted above the monitor for allowing the patient to align the shoulders before and during the corrective exercises.

15. The appliance of claim 7, wherein the polarized light screen is a vertically height adjusted screen.

16. The appliance of claim 7, wherein the polarized light screen further includes a top edge, and wherein a shelf is mounted horizontally at the top edge of the polarized light screen, to allow the patient to push against the shelf with the patient's head in order to stretch the spine during performing corrective exercises, the shelf being height adjustable.

17. The appliance of claim 7, further comprising a first pair of thrusting elements, positioned symmetrically at both sides of the polarized light screen for being pushed by the patient's trunk towards either the left or the right, according to required corrections.

18. The appliance of claim 17, further including a second pair of the thrusting elements positioned at a different level with the first pair; wherein the thrusting elements are height adjustable, and wherein a distance between the thrusting elements in each said first and second pair is adjusted according to the physical characteristics of the patient.

19. A method for diagnosis and treatment of scoliosis of a patient, comprising the steps of:

providing a polarized light screen having a back, a monitor in front of the screen, and a closed circuit camera behind the screen;

placing the patient between the screen and facing the monitor, such that the patient presses with his (or her) back against the screen, thereby causing immediate image of the patient's spine on the back of the screen;

filming said immediate image of the patient's spine appearing on the back of the screen by the closed circuit camera; and projecting, in real time, said immediate image on the monitor, thereby allowing the patient to identify, in real time, precise location of the scoliosis and thereby facilitating in performing corrective exercises as the patient pushes against the handles.

* * * * *

UNITED STATES PATENT AND TRADEMARK OFFICE
CERTIFICATE OF CORRECTION

PATENT NO. : 5,620,009
DATED : April 15, 1997
INVENTOR(S) : Carmelo DePasquale

It is certified that error appears in the above-indentified patent and that said Letters Patent is hereby corrected as shown below:

In column 2, line 67, change "he" to ---the---.

In column 3, line 39, change "138a" to ---13a---.

In column 3, line 58, change "r" to ---rigid---.

Signed and Sealed this

Eighteenth Day of November 1997

*Attest:*

BRUCE LEHMAN

*Attesting Officer*  Commissioner of Patents and Trademarks